(12) United States Patent
McCleane

(10) Patent No.: US 6,221,915 B1
(45) Date of Patent: Apr. 24, 2001

(54) PHARMACEUTICAL COMPOSITIONS

(76) Inventor: Gary McCleane, 58 Kensington Manor, Dollingstown BT66 7HR (GB)

(*) Notice: Subject to any disclaimer, the term of this patent is extended or adjusted under 35 U.S.C. 154(b) by 0 days.

(21) Appl. No.: 09/281,463

(22) Filed: Mar. 30, 1999

(30) Foreign Application Priority Data

Feb. 5, 1999 (GB) .................................................. 9902651
Mar. 25, 1999 (EP) .................................................. 99302319

(51) Int. Cl.$^7$ .......................... A61K 31/16; A61K 31/21
(52) U.S. Cl. ........................................... 514/615; 514/509
(58) Field of Search .................................... 514/615, 509

(56) References Cited

FOREIGN PATENT DOCUMENTS 0 663 212 A2  7/1995 (EP).

OTHER PUBLICATIONS

McCleane et al. "The addition of GTN to capsaicin cream reduces the discomfort associated with application of capsaicin alone.", Pain 1998, 78(2), 149–151.*

McCleane, G.J., et al., "The addition of GTN to capsaicin cream reduces the discomfort associated with application of capsaicin alone. A volunteer study," *Pain*, 78(2); 149–151 (1998).

"British National Formulary," *The Pharmaceutical Press*, London, 2.6, p. 90 (1986).

Berrazueta, J.R., et al., "Successful treatment of shoulder pain syndrome due to supraspinatus tendinitis with transdermal nitroglycerin. A double blind study," *Pain*, 66, 63–67 1996.

Fanciullacci, M., et al., "Responsiveness to Cutaneous Application of Capsaicin and Nitroglycerin in Cluster Headache Patients," *Cephalalgia*, 11(11), 240–241 (1991).

"British National Formulary," *The Pharmaceutical Press*, 2.6, p. 90 (1986).

Zhang, W.Y. and Li Wan Po, A., "The effectiveness of topically applied capsaicin," *European Journal of Clinical Pharmacology*, 46 (6); 517–522 (1994).

Rains, C. and Bryson, Harriet M., "Topical capsaicin: A review of its pharmacological properties and therapeutic potential in post–herpetic neuralgia, diabetic neuropathy and osteoarthritis," *Drugs and Aging*, 7(4), 317–328 (1995).

International Search Report issued in corresponding PCT application on 05/02/99.

* cited by examiner

*Primary Examiner*—Theodore J. Criares
*Assistant Examiner*—Jennifer Kim
(74) *Attorney, Agent, or Firm*—Wolf, Greenfield & Sacks, P.C.

(57) ABSTRACT

The present invention relates to a pharmaceutical composition comprising a nitrate vasodilator and a compound of formula I:

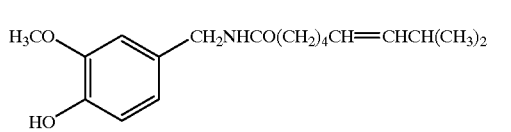

27 Claims, No Drawings

PHARMACEUTICAL COMPOSITIONS

DESCRIPTION

The present invention relates to the use of nitrate vasodilators, particularly glyceryl trinitrate, capsaicin and capsaicin like compounds as analgesics.

The analgesic properties of topical chilli pepper preparations have been known for sometime. For example, in 1850 the use of such preparations in the treatment of chilblains (Turnbull A., Dublin Med. Press 1850; 95–6.) was reported. It seems that this analgesic effect can be attributed to the capsaicin-containing fraction of the chilli pepper and that this effect is, at least in part, mediated by the ability of capsaicin to reversibly deplete unmyelinated C fibre afferent neurones of sensory neuropeptides, in particular, neuropeptide Substance P (SP) (Rains and Bryson, Drugs and Ageing 1995; 7:317–28; Fitzgerald M., Pain 1983; 15: 109–30.). As Substance P has an important role in central transmission of nociceptive or "pain" signals, its repeated depletion from afferent neurones as a consequence of the repeated application of capsaicin results in a "desensitisation" to pain. Isolated capsaicin has the chemical formula: N-(4-hydroxy-3-methoxybenzyl)-8-methylnon-trans-6-enamide.

An analgesic effect with topical application of capsaicin has been demonstrated in conditions as diverse as post mastectomy pain syndrome (Watson and Evans, Pain 1992; 51: 375–79.), painful diabetic neuropathy Tandan et al., Diabetes Care 1992; 15: 8–13.; The Capsaicin Study Group, Arch Intern Med 1991: 151: 2225–9), post-herpetic neuralgia (Watson et al., Pain 1988, 33: 333–40; Watson et al., Clin. Ther. 1993, 15: 510–26; Bernstein et al., J. Am Acad Dermatol 1989, 21: 265–70.) and pain in Guillian-Barre syndrome (Morganlander et al, Annals of Neurology 1990, 29:199). Capsaicin has also been used in the treatment of osteoarthritis (Deal et al., Clin Ther 1991, 13: 383–95; McCarthy and McCarty, J. Rheumatol 1992, 19: 604–7; Altman et al., Seminars in Arthritis and Rheumatism 1994, 23: 25–33.). The symptoms of osteoarthritis include the destruction of joint architecture and are almost a natural accompaniment of advancing age. Thus, the therapeutic aim in treating this condition is largely to palliate symptoms and to maximise quality of life. Patients suffering from conditions such as osteoarthritis, for which the use of a topical preparation of capsaicin is known to have an effect, generally, will have tried the first line of treatment "over the counter" preparations and will then have progressed to the use of codeine based drugs and anti-inflammatories. However, these available therapeutic agents are limited by side effects such as gastric bleeding with non-steroidal anti-inflammatory agents (Blower et al., Aliment Pharmacol Ther 1997; 11: 283–91.) and analgesic tolerance with codeine based preparations. It is probable, therefore, that capsaicin will have been used in situations where conventional analgesia has either failed to have an effect or has created side effects. It, therefore, would be undesirable for an agent kept in reserve for such a situation to itself be prone to cause side effects which may necessitate termination of treatment prior to a point where analgesia is apparent.

Unfortunately, topical application of capsaicin, especially initially, is associated with burning discomfort at the application site and this prominent side effect compromises the efficacy of the treatment. The Capsaicin Study Group reported that 87 of 138 patients in their study suffered burning discomfort after application of 0.075% capsaicin, while Watson and colleagues (Clinical Therapeutics, 1993, 15:510–26) reported that 9 of 33 patients in their study suffered burning after application of 0.025% capsaicin. This discomfort has lead to patients dropping out of at least one study (Watson et al. Pain 1988; 33: 333–40). The failure of patient drug compliance makes the full potential of this agent to give pain relief hard to gauge.

It would, therefore, be desirable to formulate a cream, ointment or the like for the topical application of capsaicin such that the burning discomfort on application is reduced while the analgesic properties of capsaicin are retained. It would be even more desirable if the formulation that lead to a reduction in burning discomfort could also provide an analgesic effect greater than that obtained by the application of capsaicin alone. Glyceryl trinitrate (GTN) has a long pedigree in the treatment of angina pectoris for which it is administered lingually, sublingually or bucally in the form of chewable tablets. It can also be applied to the skin in the form of a transdermal patch applied to the area in which ischaemic pain is sensed (normally the chest or arms). The predominate effect is rapid vasodilation which may be mediated through the action of GTN on cyclic guanidine monophosphate (cGMP) (Feelisch and Noack, Eur J. Pharmacol 1987; 139: 19–30.). This allows venous pooling of blood with a subsequent reduction in pressure in the ventricles and redistribution of blood to ischaemic regions and, hence, relief from the ischaemic pain.

DETAILED DESCRIPTION OF THE INVENTION

In a first aspect, the present invention provides a pharmaceutical composition comprising a nitrate vasodilator and a compound of formula I:

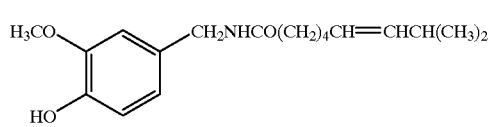

the composition being useful in a medical treatment, preferably as an analgesic.

In preferred embodiments, the composition is formulated for topical application at or in the vicinity of a source of pain or discomfort and can further comprise a pharmaceutical carrier rendering it suitable for topical application to the skin. Such carriers are well known to those skilled in the art. Suitable carriers include those employed in Axsain cream available from Bioglan Laboratories Ltd. (purified water, sorbitol solution, isopropyl mysristate, acetyl alcohol, petrolatum (white), benzyl alcohol, glyceryl stearate and PEG-100 stearate (Arlacel 165)) and those employed in the GTN ointment, Percutol (Dominion Pharmaceuticals, UK) (lanolin, white petrolatum, lactose and water). Preferably, pharmaceutical compositions in accordance with the invention are for ameliorating deep seated or internal pain which can be of skeletal or muscular origin, or emanate from a joint. In preferred embodiments, pharmaceutical compositions in accordance with the invention are useful for ameliorating pain associated with arthritis, particularly osteoarthritis.

Where compounds and compositions are said to ameliorate or to be for ameliorating pain or discomfort, it is meant that they are effective to reduce the intensity of pain, or have an analgesic effect, and, although a so described agent is preferably capable of eliminating a particular pain, it need not necessarily be capable of so doing. The term pain is used in a general sense and to encompass pain levels between the merely uncomfortable and the virtually unbearable.

In preferred embodiments of the invention, the nitrate vasodilator is present in an amount sufficient to reduce burning discomfort associated with the application of a compound of formula I to the skin. Preferably, the nitrate vasodilator is present in an amount sufficient to augment an analgesic effect provided by a compound of formula I.

Preferably, the nitrate vasodilator is glyceryl trinitrate; the preferred compound of formula I is capsaicin.

In preferred embodiments, pharmaceutical compositions in accordance with the invention comprise between 0.01 and 0.1%, preferably between 0.015 and 0.075% and, more preferably, between 0.015 and 0.035% capsaicin and between 0.5 and 2.5%, and preferably, between 0.5 and 2% glyceryl trinitrate. Such compositions can be in the form of a cream, jelly, ointment, gel, lotion, paste or for application by a patch.

Other conditions treatable with pharmaceutical compositions in accordance with the invention include post mastectomy pain syndrome, painful diabetic neuropathy and post-herpetic neuralgia.

In a second aspect, the present invention provides anD analgesic treatment comprising sequentially or simultaneously administering a nitrate vasodilator and a compound of formula I

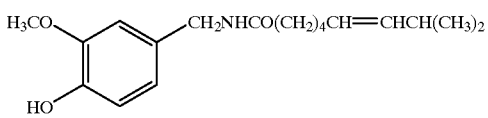

to a patient in need of analgesic treatment. The nitrate vasodilator and compound of formula I can be topically applied to the skin at or in the vicinity of a source of pain. Preferably, the nitrate vasodilator and compound of formula I are applied simultaneously in a single preparation comprising the nitrate vasodilator, a compound of formula I and a pharmaceutically acceptable carrier. Suitable carriers include those employed in pharmaceutical compositions in accordance with the first aspect of the invention.

Preferably, the analgesic treatment is to ameliorate deep seated or internal pain. The pain can be of skeletal or muscular origin, or emanate from a joint. In this last case, the pain can be associated with arthritis, particularly osteoarthritis. The pain can also be neuropathic pain, particularly post diabetic neuropathy or post-herpetic neuralgia.

In preferred embodiments of this aspect of the invention, the nitrate vasodilator is used in an amount sufficient to reduce burning discomfort associated with the application of a compound of formula I. The nitrate vasodilator can be used in an amount sufficient to augment an analgesic effect provided by the compound of formula I. The preferred nitrate vasodilator is glyceryl trinitrate and the preferred compound of formula I is capsaicin. The preparation can be a cream, jelly, ointment, gel, lotion, paste or for application by a patch.

In a third aspect, the invention provides a method of ameliorating deep seated or internal pain, comprising topically administering a nitrate vasodilator to a subject suffering said pain at or in the vicinity of the source of said pain. It is preferred that the nitrate vasodilator should be applied to the skin and that the treated pain is of skeletal or muscular origin, or emanates from a joint. In the latter case, the pain can be associated with arthritis, particularly osteoarthritis. In another embodiment, the pain can be neuropathic pain, particularly post diabetic neuropathy or post-herpetic neuralgia.

It is preferred that the nitrate vasodilator should be administered in association with a pharmaceutically acceptable carrier and, preferably, in a cream, jelly, ointment, gel, lotion, paste or for application by a patch.

The preferred nitrate vasodilator is glyceryl trinitrate.

In a fourth aspect, the present invention provides a use of a nitrate vasodilator in the preparation of a medicament for ameliorating deep seated or internal pain or discomfort in an individual, wherein the medicament is formulated for topical application in the vicinity of the source of said pain and the nitrate vasodilator has an ameliorating effect upon said pain.

In a fifth aspect, the present invention provides a use of a nitrate vasodilator and a compound of formula I in the preparation of a medicament for ameliorating deep seated or internal pain or discomfort in an individual, wherein the nitrate vasodilator has an ameliorating effect upon said pain. In a preferred embodiment of this last aspect of the invention, the medicament is formulated for topical application at or in the vicinity of the source of said pain.

In preferred embodiments of the last two aspects of the invention, the compound of formula I has an ameliorating effect upon the treated pain. A medicament prepared in accordance with the fourth aspect of the invention can be for sequential or simultaneous administration with a compound of formula I.

The preferred compound of formula I is capsaicin and the preferred nitrate vasodilator is glyceryl trinitrate. The treated pain is preferably of skeletal or muscular origin, or emanates from a joint. In this last case, the pain can be associated with arthritis, particularly osteoarthritis. In other embodiments, the pain can be neuropathic pain, particularly post diabetic neuropathy or post-herpetic neuralgia.

The medicament can further comprise a pharmaceutically acceptable carrier and can be suitable for topical application to the skin. Preferably the medicament is a cream, jelly, ointment, gel, lotion, paste or for application by a patch. Preferably the medicament comprises between between 0.5 and 2.5%, and preferably, between 0.5 and 2% glyceryl trinitrate and, when it comprises capsaicin, the medicament can include between 0.01 and 0.1%, preferably between 0.015 and 0.075% and, more preferably, between 0.015 and 0.035% capsaicin.

An advantage of those aspects of the invention which involve the use of a nitrate vasodilator alone, is that they can provide an effective topical analgesic treatment for deep seated or internal pain such as that emanating from a joint, or a muscular or skeletal source, without the attendant disadvantages associated with systemic drug treatments or the topical use of capsaicin and like compounds alone. Advantages of those aspects of the invention involving the combined use of a nitrate vasodilator and a compound of formula I include the prevention of the burning sensation normally associated with compounds of formula I and a more than additive analgesic effect. When topically applied, such combined compositions have the further advantage of not causing the side-effects associated with many systematically active drugs when administered via an oral route.

A combination of capsaicin and glyceryl trinitrate (GTN) was tested in a volunteer study, details of which are set out in Example 1 below. The results of this study show that the burning discomfort normally associated with capsaicin was reduced in individuals treated with capsaicin in combination with GfN when compared to that felt in individuals treated with capsaicin alone.

The results of a study to determine the analgesic effect and effect on tolerability of the addition of GTN to capsaicin cream in patients with osteoarthritis are described in Example 2 below. These show that both GTN and capsaicin are significantly more effective at reducing the pain of osteoarthritis when repeatedly applied to the effected joint than a placebo and that the combination of both together gives a more than additive effect when compared with a placebo. Furthermore, the results demonstrate that the discomfort caused by application of capsaicin is significantly less when it is used together with GTN and that a greater proportion of patients desire to continue using the combination of capsaicin and GTN than either alone.

Thus, analgesic benefit can be derived in patients with osteoarthritis who repeatedly apply either capsaicin or GTN creams to a painful joint and that the combination of both together is more effective and more tolerable than either alone. The significant number of patients who elected to continue on their study medication in the combined group is a testimony to its efficacy and tolerability. The patient populations studied are not a representative spectrum of adult patients with osteoarthritis pain but rather those in whom more conventional agents had either not been tolerated or had been ineffective. To have demonstrated both a statistical and clinical reduction in pain scores in this group indicates that medicaments comprising GTN or GTN and capsaicin are useful additions to the treatment options for patients with painful osteoarthritis or other conditions involving deep seated pain such as neuropathic pain, particularly painful diabetic neuropathy and post-herpetic neuralgia. A further advantage of the invention is that patients in particular are attracted to the notion of applying medication to that area which is affected. Despite an apparent medical prejudice against topical preparations (Bateman and Kennedy, BMJ 1995; 310: 817–8; Anonymous, Drug Ther Bull 1994; 32: 91–5) the experience with topical anti-inflammatory agents suggests that patients preferences in this respect are generated not only by the apparent reduction in side effects but also by real clinical efficacy (Moore et al. BMJ 1998; 316: 333–8). The lack of gastrointestinal and renal side effects represent further advantages in an often elderly population group.

EXAMPLE 1

Discomfort Associated with Topical Application of Capsaicin: A Volunteer Study

Forty healthy individuals were recruited on a voluntary basis for participation in the study. AR were aware that burning discomfort may occur after application of the preparations and that accidental transfer of the cream to other sites (e.g. eyes, nose etc.) could be associated with discomfort.

Four preparations were used: A, B, C and D:

A—Axsain Vehicle

B—Axsain Cream 0.075%[1]+GTN 2%[2] (to give 0.025% Capsaicin 1.33% GTN

C—Axsain Cream 0.075%[1]+Axsain Vehicle (to give 0.025% Capsaicin)

D—GTN 2%[2]+Axsain Vehicle (to give 1.33% GTN)

[1]Axsain Cream, Bioglan Laboratories Ltd (Capsaicin)
[2]GTN ointment, Percutol, Dominion Pharmaceuticals (UK)

0.1 ml (measured with a 2 ml syringe) of each cream was applied to a 1 inch$^2$ area (measured with a celluloid template) to the dorsum of the non-dominant hand proximal to the metacarpal pharyngeal joint on a single occasion, within a 1 day interval between application of each cream. Patients were instructed not to wash the hand for 2 hours and asked to rate their burning discomfort after 6 hours on a 0–10 visual analogue score (VAS). Patients had been divided into 4 groups of ten and the order of application was varied so as to ensure that one agent was not always followed by the same preparation.

10 subjects A - B - C - D 10 subjects D - C - B - A 10 subjects C - A - D - B 10 subjects B - D - A - C Neither investigator nor subject was aware of the constituents of the applied cream. Non parametric tests were used for VAS results and $p<0.05$ considered statistically significant.

RESULTS

Results were obtained from all 40 participants. Apart from burning or itching at the site of application of the creams no other side effects were apparent.

| Group | Constituent of cream | VAS: median (range) | Difference from Capsaicin (Group C) |
|---|---|---|---|
| A | Axsain Vehicle (placebo) | 0 (0–6) | P < 0.001 |
| B | Capsaicin 0.025% + GTN 1.33% | 0 (0–7) | P = 0.002 |
| C | Capsaicin 0.025% | 3 (0–7) | |
| D | GTN 1.33% | 0 (0–2) | P 0.001 |

The results of this double blind, placebo trial of 40 volunteers show the burning discomfort associated with application of capsaicin cream (0.025%) compared to placebo, GTN cream (1.33%) and to the combination of capsaicin cream (0.0250%) plus GTN cream 1.33%. Median VAS for burning pain were 0 for the placebo, GTN and GTN+capsaicin groups and 3 for the capsaicin group after single application of each cream at daily intervals. This demonstrates that after a single application, the addition of GTIN to capsaicin significantly reduces the burning discomfort associated with the application of capsaicin alone.

EXAMPLE 2

The Effects of Topical Capsaicin and GTN in Patients with Painful Osteoarthritis: a Randomised, Double Blind, Placebo Controlled Study Subjects: A double blind, randomised, placebo controlled trial of two hundred patients with osteoarthritis pain presenting to a District General Hospital Pain Clinic. Previous treatment with non-steroidal anti-inflammatory agents or simple analgesics was either ineffective or complicated by intolerable side effects. Those using nitrate preparations and those in whom concomitant medication was expected to change over the study period were excluded from the study. Regional research ethics committee approval was granted for the study and all patients gave informed written consent for participation in the study. Patients were randomly allocated to one of four groups (A, B, C, D) in equal numbers using a computer generated random number list. These patients received (in a double blind fashion):

Group A 0.025% capsaicin

Group B placebo (vehicle for the active agents used in the other groups)

Group C 1.33% GIN (2 parts 2% GTN, 1 part placebo)

Group D 0.025% capsaicin, 1.33% GIN (1 part 0.075% capsaicin, 2 parts 2% GTN)

All study creams were contained in a coded, but otherwise unlabelled dark glass containers (these were prepared by Bioglan Laboratories Ltd). These creams were all white in colour and odourless.

Patients were instructed to apply a volume of study cream equivalent to a grain of rice four times daily over a six week period to a single painful joint. They were further instructed not to wash that joint for at least 1 hour after cream application.

Patients were asked to record their average daily pain scores using a 0–10 linear visual analogue score ("VAS"; 0=no pain, 10=most amount of pain imaginable) and to further record their total daily analgesic consumption (number of tablets taken) and the discomfort of cream application using a 10 cm linear visual analogue score (0=no discomfort, 10=most amount of discomfort imaginable).

Analysis of Variance (ANOVA) and Regression Techniques were used to examine for the main effects of the study creams. Cusum analysis of daily means was used to provide information on where changes in patients behaviour tended to occur, and descriptive statistics of patients allocated to each treatment group. Patients desire to continue with treatment was examined using logistic regression.

167 patients provided results (83.5%). There were no statistically significant differences between the treatment groups in term of sex distribution or age (Table 1). Natural variability was seen in pain scores within 5 days of start of treatment in some groups so it was decided to compare the mean pain scores of days 1–4 ("baseline pain scores", i.e. pain scores prior to treatment effect) with the final week of treatment. Baseline VAS (0–10 scale) for pain were 4.2. One-way analysis of variance of baseline pain scores indicated no differences between treatment groups (F=0.31 on 3 and 163 degrees of freedom: p>0.05). Neither age, sex or the interaction between GTN and capsaicin were found to be statistically significant when regression analysis was used. However, baseline level of pain of individuals was significantly associated with the ability to change (those with high scores initially showed more propensity to improve).

The mean pain scores after 42 days and the results of the regression analysis are shown in Table 2. There was a significant reduction in pain scores in the GTN group (mean decrease 0.59, p>0.05), the 0.025% capsaicin group (mean decrease 0.5, p<0.05) and in the capsaicin and GTN group (mean decrease 1.1). The decrease in mean pain score beyond that given by the cream vehicle (placebo) alone was 0.28 in the capsaicin group, 0.37 in the GTN group but 0.88 in the group treated with both agents. Combining the active agents, therefore, provided a greater than additive effect.

The Kurskal—Wallis One-way Analysis of variance of ranks indicated significant differences between treatment groups in terms of discomfort of application. ($x^2$=24.91 on 3 degrees of freedom; p<0.001). Those allocated to the capsaicin group appeared to have worse baseline discomfort (Table 3) the score being higher by 2.1 units (p>0.001). GTN and the placebo had an equal effect in terms of application discomfort: marginal initial discomfort which changed by a coefficient of 0.33 with time. As shown in Table 3, the GTN/capsaicin group had the lowest baseline discomfort of all at −1.26 (p<0.05).

Only these baseline discomfort scores were found to be statistically significant in regression analysis. Discomfort of application scores fell by about a third of their original values over the six week period, irrespective of the treatment (see Table 4). However, with the capsaicin only group, this fall is from a higher initial level (2.1 units higher) than for the other groups. Thus, the addition of GTN to capsaicin reduces discomfort both at the onset and throughout treatment.

One-way Analysis of variance of daily usage (tablets) of analgesic in week 1 indicated no differences between treatment groups (F=0.60 on 3 and 163 degrees of freedom; p>0.05). There was a significant reduction in usage of analgesics for people treated with GTN, capsaicin and GTN/capsaicin, falling from an initial mean of 4 tablets daily by 0.48 in the GTN and GTN/capsaicin groups (p<0.01) and 0.28 in the capsaicin group (p>0.05). See Table 5.

Patients' desire to continue with current treatment is shown in Table 6. The percentage of patients who wished to continue with treatment was 24.4% and 27.5% in the Capsaicin and GTN treatments groups respectively but 35.7% in the GTN/capsaicin group. The percentage of patients wishing to continue the treatment was significantly greater, therefore, in the patient group receiving the combination.

TABLE 1

Patients characteristics

| Treatment | Males | Females | Mean Age |
|---|---|---|---|
| Placebo | 16 (40%) | 24 (60%) | 48.4 |
| Glyceryl Trinitrate | 22 (49%) | 23 (51%) | 48.1 |
| Capsaicin | 23 (58%) | 17 (42%) | 49.7 |
| GTN + Capsaicin | 17 (41%) | 25 (59%) | 50.9 |
| All | 78 (47%) | 89 (53%) | 49.2 |

TABLE 2

Pain changes resulting from treatment (Baseline Pain Score = 4.2)

| Treatment | Mean Pain Score after 42 days (VAS) | Reduction in pain score (VAS) | Reduction in pain score (VAS) compared to placebo |
|---|---|---|---|
| Placebo | 3.98 | 0.22 | 0 |
| Capsaicin | 3.70 | 0.5 | 0.28 |
| GTN | 3.61 | 0.59 | 0.37 |
| Capsaicin/GTN | 3.10 | 1.1 | 0.88 |

TABLE 3

Application discomfort - Baseline scores versus treatment

| Variable | VAS | Standard Error |
|---|---|---|
| Capsaicin | 2.1 | 0.53 |
| Capsaicin/GTN | −1.26 | 0.61 |

TABLE 4

Application discomfort - changes resulting from baseline score

| Variable | Coefficient | Standard Error | Significance* |
|---|---|---|---|
| Baseline discomfort | −0.33 | 0.07 | p < 0.01 |

* = One-tail tests on Glyceryl trinitrate and Capsaicin; Two-tail test on Baseline pain

TABLE 5

Analgesic use - changes from treatment
(Analgesic use at beginning of treatment = 4 tablets per day)

| Variable | Tablets per day after treatment | Reduction in daily tablet consumption |
| --- | --- | --- |
| Capsaicin | 3.72 | −0.28 |
| GTN | 3.52 | −0.48 |
| Capsaicin/GTN | 3.52 | −0.48 |

TABLE 6

Patients' desire to continue with current treatment

| Treatment Group | Patients wishing to continue | Patients not wishing to continue |
| --- | --- | --- |
| Placebo | 3 | 37 |
| Glyceryl Trinitrate | 11 | 34 |
| Capsaicin | 11 | 29 |
| Glyceryl Trinitrate/ Capsaicin | 15 | 27 |

EXAMPLE 3

A composition of capsaicin and GTN for topical application is formulated from the following ingredients:

| Ingredient | % w/w |
| --- | --- |
| Capsaicin | 0.025 |
| Glyceryl Trinitrate (GTN) | 1.33 |
| Lanolin | 26.7 |
| White Soft Paraffin | 20.3 |
| Lactose | 12.0 |
| Sorbitol solution 70% | 8.3 |
| Cetyl alcohol | 2.7 |
| Isopropyl myristate | 0.85 |
| Glyceryl stearate | 0.85 |
| PEG 100 stearate | 0.85 |
| Benzyl alcohol | 0.3 |
| Water | 25.795 |

The lanolin, white soft paraffin, isopropyl myristate, glyceryl stearate and PEG 100 stearate are heated and mixed together to produce a homogeneous mixture. A capsaicin/cetyl alcohol mix is then added and the bulk mixed.

Separately, an aqueous phase is prepared by heating and mixing the water, sorbitol solution and benzyl alcohol.

The oil phase is then homogenised with the aqueous phase, and the glyceryl trinitrate/lactose mix added with continued mixing as the product is allowed to cool.

EXAMPLE 4

A composition of GTN for topical application is formulated from the following ingredients:

| Ingredient | % w/w |
| --- | --- |
| Glyceryl Trinitrate | 2.0 |
| Lanolin | 40.0 |
| White soft paraffin | 30.0 |
| Lactose | 18.0 |
| Water | 10.0 |

The lanolin and white soft paraffin are heated and mixed together to produce a homogeneous mixture. The oil phase is then homogenised with the water, and the glyceryl trinitrate/lactose mix added with continued mixing as the product is allowed to cool.

EXAMPLE 5

A composition of capsaicin for topical application is formulated from the following ingredients:

| Ingredient | % w/w |
| --- | --- |
| Capsaicin | 0.025 |
| Lanolin | 26.7 |
| White Soft Paraffin | 20.3 |
| Sorbitol solution 70% | 8.3 |
| Cetyl alcohol | 2.7 |
| Isopropyl myristate | 0.85 |
| Glyceryl stearate | 0.85 |
| PEG 100 stearate | 0.85 |
| Benzyl alcohol | 0.3 |
| Water | 39.125 |

The lanolin, white soft paraffin, isopropyl myristate, glyceryl stearate and PEG 100 stearate are heated and mixed together to produce a homogeneous mixture. A capsaicin/cetyl alcohol mix is then added and the bulk mixed.

Separately, an aqueous phase is prepared by heating and mixing the water, sorbitol solution and benzyl alcohol.

The oil phase is then homogenised with the water phase with continued mixing as the product is allowed to cool.

What is claimed is:

1. A pharmaceutical composition comprising glyceryl trinitrate and a compound of formula I:

$$\text{OCH}_3\text{-}\underset{\text{OH}}{\text{C}_6\text{H}_3}\text{-CH}_2\text{NHCO(CH}_2)_4\text{CH}=\text{CHCH(CH}_3)_2$$

wherein the glyceryl trinltrate is present in an amount sufficient to enhance the effectiveness of the compound of formula I.

2. The pharmaceutical composition as claimed in claim 1 wherein the composition is formulated as an analgesic.

3. The pharmaceutical composition as claimed in claim 1 wherein the composition formulated for topical application at or in the vicinity of a source of pain or discomfort.

4. A pharmaceutical composition as claimed in claim 1 further comprising a pharmaceutical carrier suitable for topical application to the skin.

5. The pharmaceutical composition as claimed in claim 1 wherein the composition is formulated for ameliorating deep seated or internal pain.

6. The pharmaceutical composition as claimed in claim 1 wherein the composition is formulated for ameliorating skeletal, muscular or joint pain.

7. The pharmaceutical composition as claimed in claim 1 wherein the composition is formulated for ameliorating pain associated with arthritis, particularly osteoarthritis.

8. The pharmaceutical composition as claimed in claim 1 wherein the composition is formulated for ameliorating neuropathic pain, particularly painful diabetic neuropathy or post-herpetic neuralgia.

9. A pharmaceutical composition as claim 1, wherein the glyceryl trinitrate is present in an amount sufficient to reduce burning discomfort associated with the application of a compound of formula I to the skin.

10. A pharmaceutical composition as claimed in claim 1, wherein the compound of Formula I is capsaicin.

11. A pharmaceutical composition as claimed in claim 1 comprising between 0.01% and 0.1% of the compound of formula I.

12. A pharmaceutical composition as claimed in claim 11 comprising between 0.015% and 0.075% of the compound of formula I.

13. A pharmaceutical composition as claimed in claim 12 comprising between 0.015% and 0.035% of the compound of formula I.

14. A pharmaceutical composition as claimed in claims 11, 12 or 13 comprising between 0.5% and 2.5% glyceryl trinitrate.

15. A pharmaceutical composition as claimed in claim 14 comprising between 0.5% and 2% glyceryl trinitrate.

16. A pharmaceutical composition as claimed in claim 1 in the form of a cream, jelly ointment, gel, lotion, paste, or in a form which can be applied by a patch.

17. A method of providing an analgesic treatment comprising sequentially or simultaneousiy administering glyceryl initrate and a conpound of formula I:

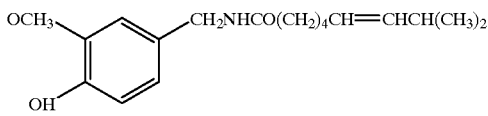

to a patient in need of analgesic treatment, wherein the glyceryl trinitrate is present in an amount sufficient to enhance the effectiveness of the compound of formula I.

18. A method as claimed in claim 17, wherein the glyceryl, trinitrate and compound of formula I are in a form for being topically applied to the skin at or in the vicinity of a source of pain.

19. A method as claimed in claim 18, wherein the glyceryl trinitrate and compound of formula I are applied simultaneously in a single preparation comprising the glyceryl trinitrate, the compound of formula I, and a pharmaceutically acceptable carrier.

20. A method as claimed in claim 18, wherein the glyceryl trinitrate and compound of formula I are applied in separate preparations.

21. A method as claimed in claim 17, wherein the analgesic treatment is to ameliorate a deep seated or internal pain.

22. A method as claimed in claim 21, wherein the analgesic treatment is to ameliorate skeletal, muscular or joint pain.

23. A method as claimed in claim 22, wherein the analgesic treatment is to a meliorate pain associated with arthritis, particularly osteoarthritis.

24. A method as claimed in claim 17, wherein the analgesic treatment is to ameliorate neuropathic pain, particularly painful diabetic neuropathy or post herpetic neuralgia.

25. A method as claimed in claim 17, wherein the glyceryl trinitrate is used in an amount sufficient to reduce burning discomfort associated with the application of a compound of formula I.

26. A method as claimed in claim 17, wherein the compound formula I is capsaicin.

27. A method as claimed in claim 19, wherein said preparation is a cream, jelly, ointment, gel, lotion, paste, or in a form which can be applied by a patch.

* * * * *